United States Patent [19]

Russell

[11] Patent Number: 5,137,833
[45] Date of Patent: Aug. 11, 1992

[54] METHOD FOR DETECTING POLYHYDROXYL COMPOUNDS

[76] Inventor: Anthony P. Russell, 173 Union Ave., Sudbury, Mass. 01776

[21] Appl. No.: 410,657

[22] Filed: Sep. 21, 1989

[51] Int. Cl.$^5$ .................. G01N 23/06; G01N 33/50
[52] U.S. Cl. ..................................... 436/94; 436/131; 436/172; 534/694; 534/692; 534/713; 534/726
[58] Field of Search .................. 534/573 P, 582, 583, 534/692, 694, 713, 726; 436/95, 57, 94, 172, 800, 131

[56] References Cited

U.S. PATENT DOCUMENTS

| | | | |
|---|---|---|---|
| 2,112,244 | 3/1938 | Jurist | 534/694 |
| 2,496,151 | 1/1950 | Dawson et al. | 534/582 X |
| 4,269,605 | 5/1981 | Dean et al. | 436/67 |
| 4,308,254 | 12/1981 | Tayot et al. | 436/529 X |
| 4,371,374 | 1/1983 | Cerami et al. | 436/87 |
| 4,621,049 | 11/1986 | Wang | 435/805 |
| 4,659,817 | 4/1987 | Gallop et al. | 534/726 X |
| 4,820,636 | 4/1989 | Hill et al. | 435/14 |
| 4,861,728 | 8/1989 | Wagner | 436/525 X |

FOREIGN PATENT DOCUMENTS 3720736 1/1989 Fed. Rep. of Germany .

OTHER PUBLICATIONS

Glazer, *Chemical Abstracts*, vol. 68, No. 111805q (1968).
Kirk-Othmer, Encyclopedia of Chemical Technology, 3rd ed., vol. 8, John Wiley and Sons, New York, pp. 201-203 (1979).
Purokoski, Lajunen & Hakkinen, *A Potentiometric Study on The Complex Formation of Arsenious Acid, Arsenite Ion, Telluric Acid and Tellurate Ion with Sugar Acids and Disaccharides in Aqueous Solution*, Chemical Abstracts, vol. 107, No. 122178n (1987).
Hakkinen, Lajunen & Purokoski, *A Potentiometric Study on The Complex Formation of Lactitol and Maltitol with Some Inorganic Oxyacids In Aqueous Solution*, Chemical Abstracts, vol. 110, No. 83116f (1989).
Hakkinen, Purokoski & Lajunen, *A Potentiometric Study on The Complex Formation of Germanic Acid and Germanate Ion with Sugar Acids and Disaccharides in Aqueous Solution*, Chemical Abstracts, vol. 105, No. 233265s (1986).

*Primary Examiner*—Mary C. Lee
*Assistant Examiner*—Fiona T. Powers

[57] ABSTRACT

A method for detecting and measuring the concentration in solution of polyhydroxyl compounds, such as sugars. The invention makes use of certain dyes that, when linked to a derivative of boronic acid (or boronate ion), arsenious acid (or arsenite ion), or germanic acid (or germanate ion), exhibit quantitative responses to the presence of polyhydroxyl species.

12 Claims, 6 Drawing Sheets

B = 0.1 M PHOSPHATE BUFFER, pH 11.4
G = GLUCOSE, 15 MG/ML IN BUFFER, pH 11.4

METHOD FOR DETECTING POLYHYDROXYL COMPOUNDS

BACKGROUND OF THE INVENTION

A. Field of the Invention

The invention relates generally to the field of sugar-sensitive reagents, and in particular to a class of boronic, arsenious, germanic and telluric acid derivatives that exhibit quantitative sensitivity to the presence of certain polyhydroxyl compounds.

B. Description of the Related Art

Reactions of glucose and other monosaccharides play a virtually universal role in the metabolic pathways of living organisms. Chemical breakdown of monosaccharides provides a source of energy during periods of activity, while absorption and concatenated storage of these same substances takes place during quiescence. Detecting the presence and concentration of biologically important sugars in mixed aqueous solutions is necessary in a variety of industrial, medicinal and research contexts, ranging from assessing the status of fermentation processes to monitoring blood glucose levels in individual suffering from diabetes.

A number of sugar-detection methods are presently in use, but all present certain disadvantages. Enzyme sensing systems offer specificity, but contain labile protein complexes that denature upon exposure to harsh conditions (such as those encountered during steam sterilization). Refractive index methods of sugar sensing do not require special reactive conditions, but are nonspecific with respect to the chemical identity of the sugar, and tend to exhibit cross-sensitivity to other compounds, such as proteins.

The present invention makes use of the well-known ability of boric acid (and the borate ion) to bond covalently to polyols containing vicinal hydroxyl groups. Borate columns are frequently used to separate different sugars, which bind to such a column with differing strengths depending on the sugars' molecular structures; glucose typically binds most strongly of all common monosaccharides to such columns. The covalent bond formed during binding resists the influence of most contaminants, but is nonetheless reversible, thereby permitting elution with borate buffer.

Japanese Patent No. 81 116,754 describes the synthesis of dyes with diazotized m-aminophenylboronic acid (APB) and naphthol derivatives. These dyes bind to textiles containing hydroxyl groups, and exhibit absorbance maxima around 500 nm. A recent publication [Burnett, Peebles & Hageman, 96 *Biochemical and Biophysical Research Communications* 157 (1980)] discloses a fluorescent dye derived from APB and dansyl chloride, which was synthesized to bind to bacterial cell surfaces. At pH 8.5, the dye appears to have an absorbance maximum around 350 nm, and an emission maximum around 550 nm. Neither reference suggests the use of the compounds disclosed therein to detect or measure the presence of specific polyhydroxyl compounds.

DESCRIPTION OF THE INVENTION

Summary of the Invention

The present invention relates to a class of dyes that exhibit quantitative sensitivity to the presence of certain polyhydroxyl compounds. This sensitivity is expressed by diminished radiation absorbance and, in some cases, weaker fluorescence as a function of increased concentration of the polyhydroxyl compound(s), and is reversible. In accordance with the present invention, one of a variety of dye molecules is bound to a derivative of boronic acid (or boronate ion), arsenious acid (or arsenite ion), or germanic acid (or germanate ion), which bind to the vicinal hydroxy groups of compounds containing such groups. Without being bound to any particular theory or mechanism, it appears that the spectral characteristics of these dye-acid compounds become markedly attenuated when coupled to certain polyhydroxyl molecules; as the concentration of such molecules increases, a greater proportion of dye will bind thereto, resulting in a decreased spectral response.

In the preferred embodiment, the active binding moiety is an aryl compound such as APB, m-aminophenylarsenious acid, m-aminophenylgermanic acid, or m-aminophenyltelluric acid. This compound is first diazotized and then coupled to a molecule containing an electron-donating species. These reactions are exemplified as follows:

Diazotization:

Diazo Coupling:

where Ar denotes an aryl compound, Ph denotes a phenyl group, and E: is an electron donor; for example, Ph-E: can be an undiazotized amino compound such as aniline.

The dyes described herein have been synthesized to react preferentially with glucose although they respond to other polyhydroxyl species as well. It has been found that glucose sensitivity is promoted by carrying out the diazo coupling reaction in an alkaline medium rather than in acid (which is standard in the art). When exposed to glucose, the dyes respond by loss of intensity of color. This effect is due to spectral differences in the bound species as compared to free dye molecules. The dyes are also sensitive to pH. The Examples below describe the preparation of dyes responsive to glucose over a pH range of 6.5 to 13. Although boronic acid examples are set forth, similar results would be expected for analogous arsenious, germanic and telluric acid derivatives, which are known to bond to polyol compounds. See, e.g., Roy, LaFerriere & Edwards, 4 *J. Inorg. Nucl. Chem.* 106 (1957).

Detection techniques that make use of the dyes of the present invention can take a number of forms. The simplest system consists of a sample carrier, a source of radiation, and a detector capable of measuring the intensity of radiation passing through the sample. The absorbance characteristics of the dye as a function of glucose concentration at a given pH are easily established (representative response curves are depicted in the accompanying figures and discussed in the Examples relating thereto), permitting ready evaluation of a sample of unknown concentration. A treated glass surface can be used as a carrier for dyes capable of attachment to the surface molecules.

Alternatively, the dyes can be used in conjunction with standard flow injection analysis methods, in which reagents are introduced into a flowing stream of sample liquid. So long as the detector and source of radiation are placed a sufficient distance from the point of injection of the dye to permit its dispersion within the sample liquid, accurate results should be obtainable.

Another technique involves attachment of dye molecules to lengths of fiber-optic material, which are exposed to radiation and analyzed after contact with the sample. It is known that accurate absorbance spectra of colored molecules may be obtained by this method (see, e.g., Russell & Fletcher, 170 Analytica Chimica Acta 209 (1985)), and so provide the same information as that obtained from transmission spectra as discussed below.

The molecule also can be bound to polymeric material such as test paper for visual inspection. This arrangement would facilitate glucose measurement in a manner analogous to determining pH with the venerable strip of litmus paper.

EXAMPLES

The foregoing description of the invention will be understood more readily from the following Examples, when taken in conjunction with the accompanying figures referenced therein.

EXAMPLE 1

This Example illustrates preparation of a dye having a useful pH range of 6.5 to 8.5. The dye is synthesized by diazotizing an acid solution of APB with 0.5 equivalents of sodium nitrite. Under these conditions only about half of the APB is diazotized. On making the solution alkaline with sodium hydroxide (or any other compound producing hydroxyl ion upon dissociation), the diazotized molecules react with the remaining undiazotized APB, thereby forming a dye.

Synthesis 0.8 mmol of APB (110 mg) was dissolved in 3 ml of 0.3 N HCl. 0.4 mmol of $NaNO_2$ (27.6 mg) was dissolved in 1 ml of water. Both were chilled in an ice bath and mixed, which caused approximately half the APB to diazotize. After 10 min. the solution was mixed with 3 ml of 0.6 N NaOH. The diazotized APB reacted with undiazotized molecules, and the solution turned deep red. Prior to use, the dye solution was neutralized.

Properties

Figure 1:
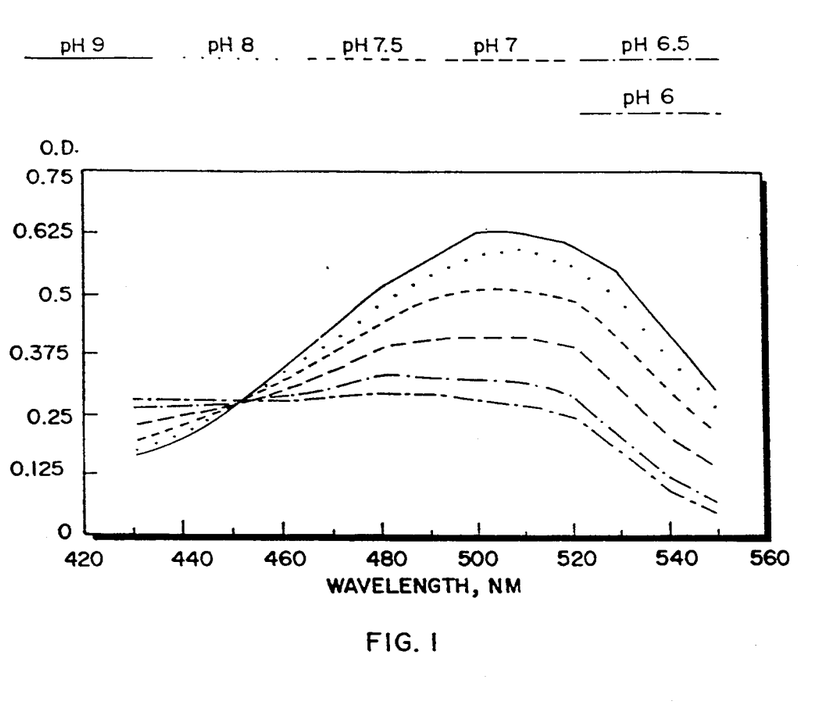

This dye has an absorbance maximum at 513 nm. An isosbestic point, the wavelength at which absorbance does not vary with pH, occurs at 443 nm. At pH 9 the dye is magenta, and below pH 6, yellow. Variation of the spectrum of the dye with pH is shown in FIG. 1, wherein O.D. indicates optical density, i.e. the logarithm of the intensity of the incident radiation divided by the intensity of the transmitted radiation. The pK of the dye is 7.5.

The dye responds to glucose over a pH range of approximately 6.5 to 8.5. To measure the response of the dye to glucose, 3 ml of the dye solution were combined with incremental amounts of 1 M glucose (10 to 50 μl). The dye and glucose stock solution both contained 0.1 M phosphate buffer to equalize the respective pH levels. The absorbance was measured at the maximum and isosbestic wavelengths. Dilution attributable to the addition of the glucose solution was corrected by taking the ratio of the absorbance of the dye at the wavelengths of its maximum and isosbestic absorbances (513 nm and 443 nm, respectively). Beer's Law dictates that the absorbance of the dye at any wavelength will equal the extinction of the dye at that wavelength multiplied by the concentration of the dye; accordingly, the concentration terms cancel when the ratio is calculated.

Figure 2:
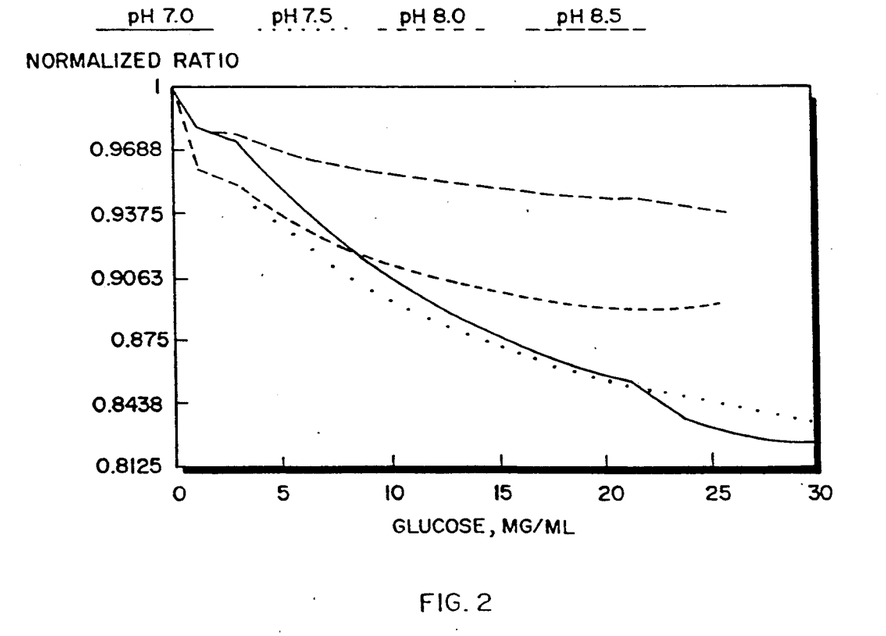

The response of the dye to glucose between pH 7 and 8.5 is shown in FIG. 2. To permit comparison between the curves, the absorbance of the dye at different pH levels has been normalized to 1 prior to the addition of glucose. The dye is most sensitive to glucose between pH 7 and 7.5.

Similar experiments were performed to test the sensitivity of the dye to sucrose a disaccharide, fructose, and mannose, both monosaccharides, and glycerol, a trihydric compound having a sugar-like composition. The dye was found to be least sensitive to sucrose and most sensitive to fructose, following the sensitivity series: sucrose < glycerol < mannose < glucose < fructose. Normalizing the sensitivity of the dye to glucose, the dye's relative sensitivity to sucrose was found to be 0.1; to glycerol, 0.4; to mannose, 0.6; and to fructose, 3.6. Consequently, the dye responds to the affinity of the boronate group for a particular sugar or polyhydroxyl compound.

Figure 3:
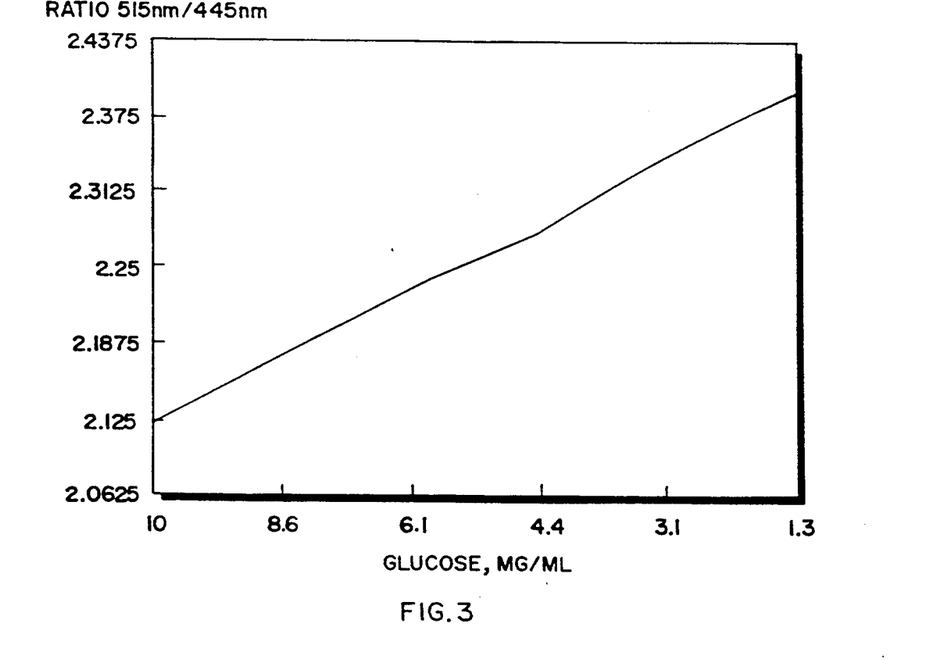

Because this dye is soluble, the reversibility of the binding of glucose thereto can be evaluated spectrally only by measuring the absorbance of the dye in the presence of glucose, and then diluting the glucose with buffer; this procedure also dilutes the dye. It is found that the ratio of the absorbances at 513 nm and 443 nm increases as the glucose concentration is lowered, indicating that the binding of glucose to the dye is reversible. This relationship is depicted in FIG. 3.

To test the usefulness of the dye as a glucose monitoring agent for fermentation processes, the dye was tested in a beef-broth solution similar to that used for the growth of bacteria. The commercial broth used contained proteins, lipids, salts, as well as 4.4 mg/ml of sugar of unknown composition. The broth was titrated to pH 7.70, and a 1 M glucose solution was brought to the same pH. The broth was colored; it had an absorbance of 1.50 at 513 nm and 1.8 at 443 nm. 3.0 ml of broth with added dye was placed in a sample cuvette and 3.0 ml of broth without dye was placed in a reference cuvette. Each cuvette was agitated. The absorbance of the sample was measured at 513 nm and 443 nm, and the ratio of the absorbance at the two wavelengths was calculated.

Figure 4:
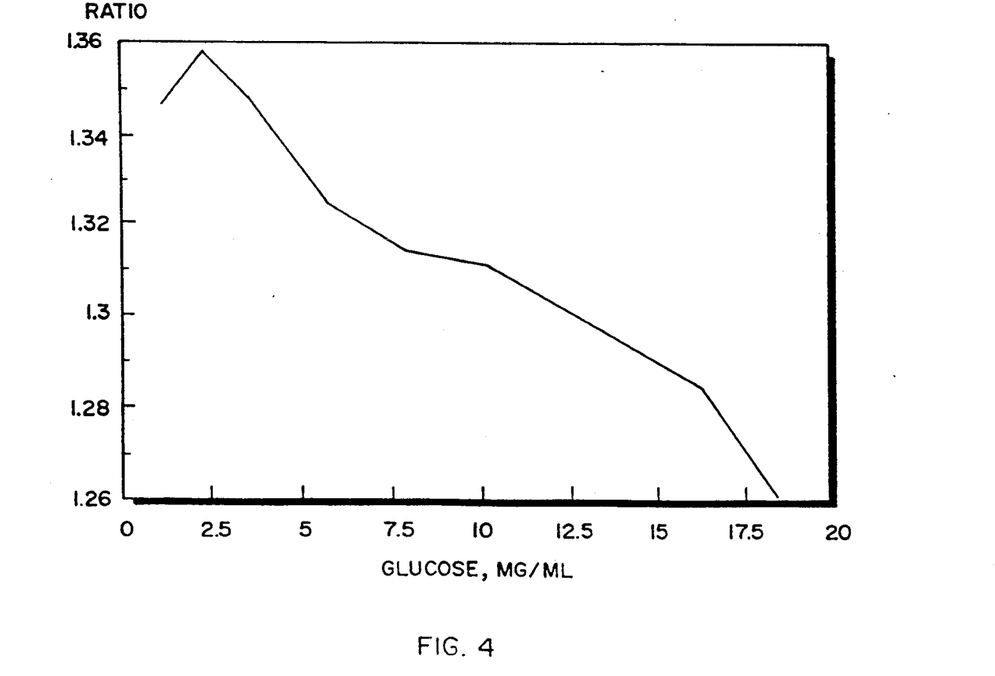

The change in this ratio as a function of glucose added both to the sample and to the reference cuvette is depicted in FIG. 4. The high absorbance of the sample and the cuvettes decreases the precision of measurements, but the data of FIG. 4 clearly show that the ratio decreases with addition of glucose, as is typical for this dye. Therefore, the response of the dye to glucose was determined suitable to permit its use in the presence of salts, proteins and lipids found in broth and other biological media over a variety of concentration levels.

To test the resistance to steam sterilization, a solution of dye was autoclaved for one-half hour. The dye solution was then tested at pH 7.5 with glucose, and found to respond in the manner depicted in FIG. 2.

EXAMPLE 2

This example illustrates synthesis of a dye having a useful pH range of 10 to 12 on a glass surface, such as that used in an optical sensing instrument. The glass surface is treated with a silanizing agent to covalently bond free amine groups thereto. Poly(allylamine sulfanilamide), from which the dye is synthesized, is then dried on the modified glass surface. The amine portions of this polymer are diazotized by dipping the glass in a chilled solution of sodium nitrite. Since the polymer has been dried to a film on the surface, the diazotization proceeds slowly, with the result that the polymer is both diazotized, cross-linked, and possibly bonded to the amines on the glass surface. The polymer is converted to a dye by dipping the glass in an alkaline solution of APB, which combines with the remaining diazo groups on the polymer.

Synthesis

Poly(allylamine sulfanilamide) is synthesized from poly(allylamine) and acetamidobenzenesulfonyl chloride by a variation of a method developed by Dawson, Gless & Wingard, Jr. [98 JACS 5996 (1970)] for the synthesis of polysulfanilamide. 1.66 g of poly(allylamine) which contained 17.6 mmol of amine groups were dissolved in 14 ml of water. 1.5 ml of 8 N NaOH were added to bring the pH to 10. 7 ml of tetrahydrofuran (THF) were added to promote co-solubility of the polymer and sulfonyl chloride during reaction. 1.51 g of p-acetamidobenzenesulfonyl chloride was added to the stirred solution, and 8 N NaOH was added as required to maintain the pH between 9 and 10. After 5 min. a further 1.51 g of the p-acetamidobenzenesulfonyl chloride was added, along with 7 ml of THF. This procedure was repeated a third time. The solution separated into two phases, a lower water-rich phase, and an upper THF-rich phase containing poly(p-acetamido-N-propylbenzene-sulfonamide). The polymer was precipitated from the THF with ethanol, washed with ethanol, and dried. Recovery was 73% of the theoretical weight of the polymer. The polymer was dissolved in 30 ml of 1 N HCl and heated at reflux for 6 h. to produce the poly(allylamine sulfanilamide).

A 2.5 cm ×2.5 cm ×0.1 cm glass plate was treated to place amine groups on the surface by soaking it in a 95% ethanol solution which contained 3-aminopropyl triethoxysilane. After 2 min. the plate was rinsed in ethanol and stored for 24 h. at room temperature to permit the silane layer to cure. One surface of the glass plate was then coated with the poly(allylamine sulfanilamide) polymer solution and drained, and the resulting polymer film was then allowed to dry at room temperature. The plate was then chilled in a glass beaker in an ice bath.

The poly(allylamine sulfanilamide) was diazotized by immersion of the glass plate in 5 ml of chilled 0.1 N HCl which contained 40 mg of $NaNO_2$. After 2 min. this solution was decanted, and 5 ml of a cold 0.6 N solution of NaOH containing 40 mg of APB was poured on the plate. The film immediately turned red from the formation of the dye. After 1 min. the plate was transferred to water. The dye film was found to be resistant to abrasion and adherent to the glass.

Properties of the Dye Film

To permit spectral studies, a cuvette for holding the glass plate with the dye film was machined out of Lucite. The cuvette was rectangular, approximately 3 cm square, with glass end-plates. The Lucite was grooved to allow the dyed plate to be inserted therein and held in the light beam. The top of the cuvette was open so that solution, which bathed the dyed plate, could be changed. The cuvette was designed to fit into the cell holder of a dual-beam spectrophotometer (Perkin-Elmer 124D) for recording the transmission spectrum of the film.

Figure 5:
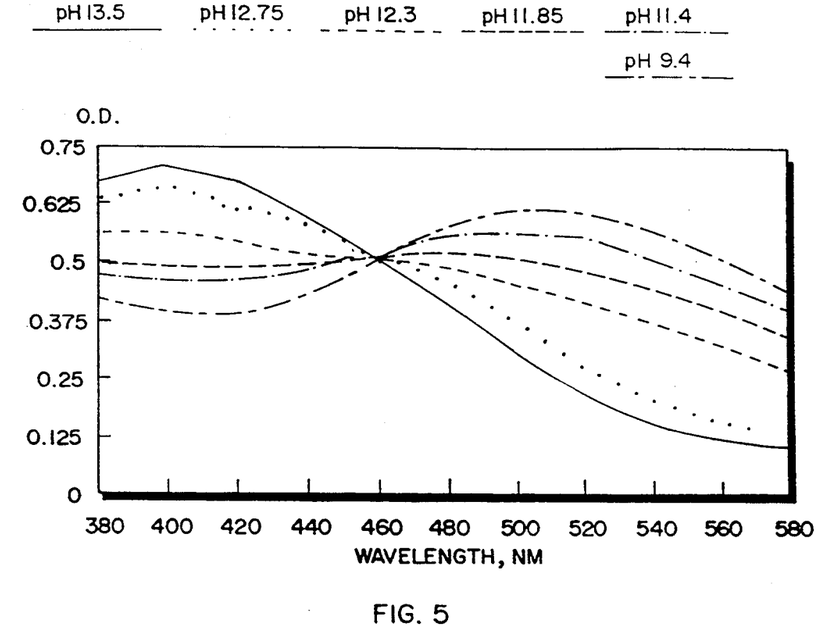

Utilizing this arrangement, the spectrum of films of this dye were recorded. The dyed film had an absorbance maximum of 500 nm, with an isosbestic point at 463 nm. The film was magenta at pH 9 and amber at pH 13. The pK was 12.2. The spectrum of the film at different pH levels is shown in FIG. 5.

Figure 6:
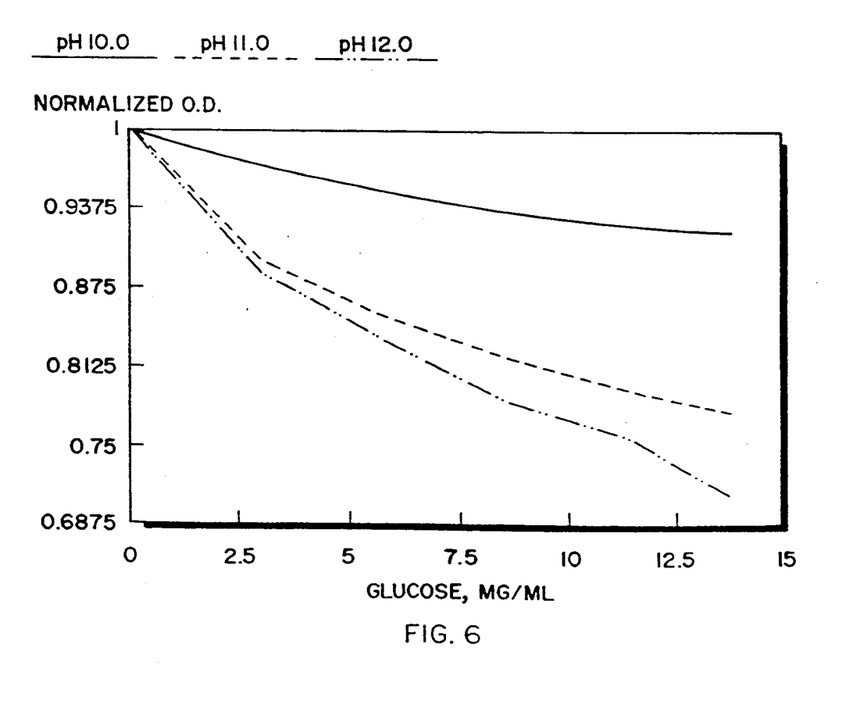

The color of the film responded to glucose at pH 10, 11, and 12. This is illustrated in FIG. 6, where the absorbance of the film at different pH levels is plotted against the concentration of added glucose at the same pH. To permit comparisons, the absorbances of the film have been normalized to 1 in the absence of glucose. The film was found to be most sensitive to glucose at pH 12, and least sensitive at pH 10. After the final addition of glucose, the film was soaked in buffer of the same pH as the measurement (but without glucose) to measure reversibility. The film was found to return to within 1–4% of the starting absorbance.

Figure 7:
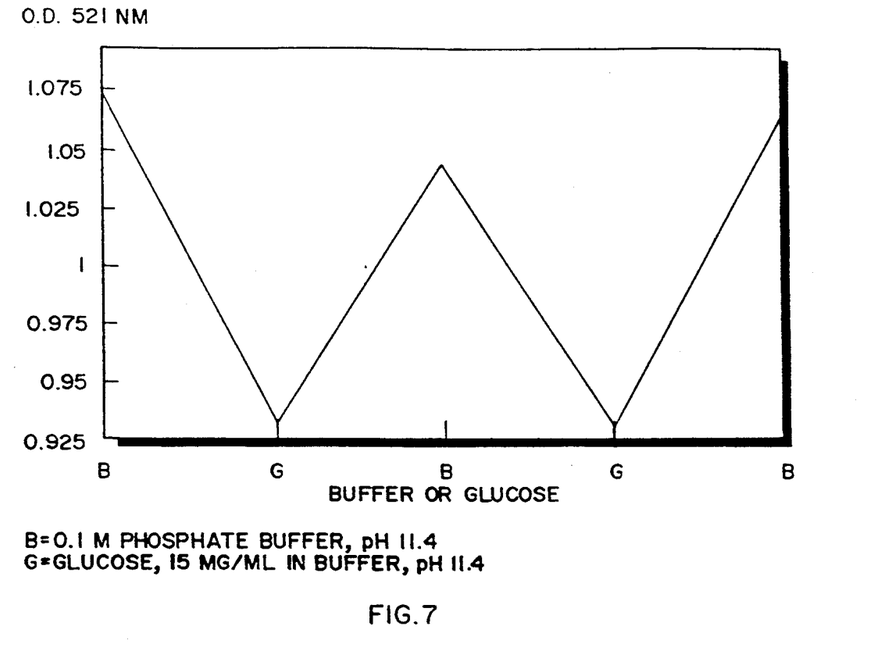

As a further test of reversibility, the film was cycled between 0.1 M phosphate buffer, pH 11.4, and 15 mg/ml glucose in the same buffer and at the same pH (phosphate buffer may be used at this pH, because the pK of the third dissociation constant of phosphoric acid is 12.67). The results appear in FIG. 7, and indicate that the change in absorbance is reversible.

EXAMPLE 3

A polymeric dye with a pK near 7.5 may be synthesized from polystyrene, or a copolymer such as styrene-maleic anhydride. The styrene is nitrated with nitric acid. The resulting nitro group is reduced with tin chloride to an amine, which is then coupled to diazotized APB to form the dye. The reaction may be performed on the polymer in solution, or directly on the surface of solid polystyrene.

Synthesis

The synthesis of nitropolystyrene maleic anhydride is adapted from the method taught in U.S. Pat. No. 2,274,551. 0.5 g of a 1:1 copolymer of styrene and maleic anhydride (SMA) was added to 2.5 ml of fuming $HNO_3$, and heated between 85° and 100° C. for 1 h. The solution was cooled, diluted with 2.5 ml of concentrated $HNO_3$, and slowly poured into 60 ml of rapidly stirred distilled water. The precipitate of nitrated SMA was recovered by filtration. The polymer was dissolved in acetone, and reprecipitated in acidified water. To reduce the nitro groups to amine groups, the polymer was dispersed in 10 ml of 2 N HCl and placed in a 100 ml flask. 0.35 g of powdered tin were added, and the mixture refluxed at 100° C. for an hour. A further 0.35 g tin and 3.5 ml of concentrated HCl were added, and refluxing was continued for 2 hours. The solution was observed to be tan in color with a small amount of brown precipitate, which was removed by centrifugation. The polymer was precipitated from the acid solution by pouring into 150 ml of acetone. The precipitate was allowed to settle, then washed with a further 75 ml of acetone, and collected on a nylon filter. After drying, the styreneamine-maleic anhydride polymer (PSAMA) was observed to be light tan.

A dye was synthesized by dissolving 6 mg of APB in 1 ml of 0.5 M HCl. After chilling, the APB received 1.1 equivalents of $NaNO_2$ in 1 ml of water. One minute later, the diazotized APB was added to 2 ml of an aqueous solution of 20 mg PSAMA that was 0.6 N in NaOH.

The solution immediately turned red. The reaction was allowed to proceed for one hour at room temperature. The dye solution was then precipitated by pouring it into 25 ml of acetone. Over a period of 2 hours, the dye settled out as a brown-red oil. The oil was dissolved in 5 ml of water, which turned deep red.

Figure 8:
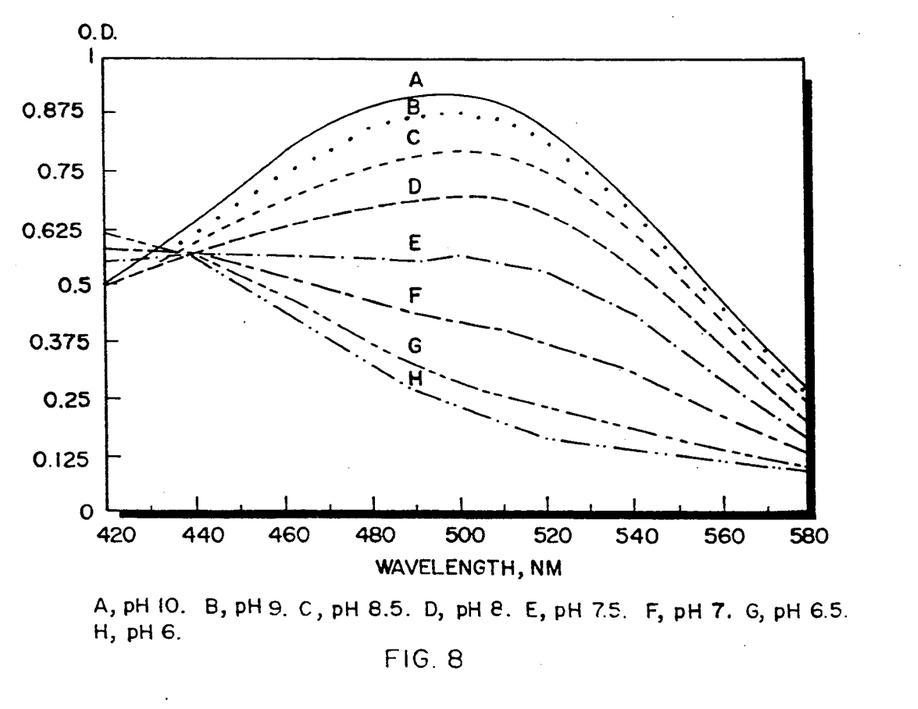

Properties 0.3 ml of the dye was dissolved in 20 ml of 0.1 M phosphate buffer. The pH of the solution was adjusted by adding small amounts of 6 N HCl or NaOH, and spectra were recorded. These spectra are depicted in FIG. 8. The maximum of absorbance occurs near 500 nm. The pK of the dye is 7.6.

Figure 9:
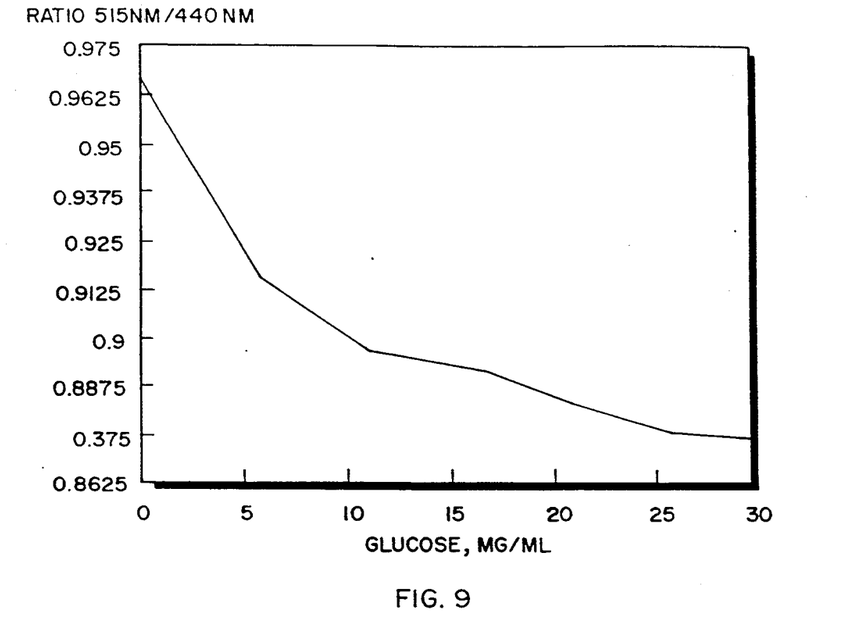

The response of the dye to glucose was measured by the method described in Example 1. 1 M glucose in 0.1 M phosphate buffer was added to a dye solution containing the same buffer. The pH of both solutions was 7.50. The ratio of the absorbances at 515 nm (where the color change was greatest) to 440 nm was calculated, and is shown in FIG. 9.

The dye is also fluorescent, with emission peaks at 380, 500 and 580 nm.

Alternatively, polystyreneamine may be synthesized from low-molecular-weight polystyrene (although commercial samples often must first be purified by dissolution in acetone and precipitation in water). The nitrated polymer forms a gummy mass which is difficult to reduce. Polystyrene from a beverage glass has been found more suitable than some commercial samples. Dyes prepared from polystyrene are not as soluble as those prepared from the styrene-maleic anhydride copolymer. The pK of the dye synthesized from polystyrene is 8–8.5. A dye may also be synthesized directly on solid polystyrene by nitrating the surface for 1–5 sec. with fuming nitric acid at room temperature, and then proceeding with reduction of the nitro groups and coupling with azo-APB as described above with respect to polystyrene maleic anhydride.

EXAMPLE 4

This example illustrates synthesis of a dye useful at pH levels of 9 to 11. The dye is synthesized from diazotized p-aminobenzoic acid and APB. 100.12 mg of p-aminobenzoic acid was dissolved in 1 ml of water. Upon chilling the solution, the aminobenzoic acid crystallized. The crystals partially dissolved when the solution was brought to 0.6 N in HCl. 1.1 equivalents of $NaNO_2$ were added, which resulted in the formation of a brown, chalky material. 100 mg of APB (equimolar with respect to the aminobenzoic acid) in 1 ml of 0.9 N NaOH was added to the solution, which then turned dark red. After 0.5 h the solution was neutralized.

Properties

3 μl of the dye were suspended in 25 ml of 0.05 M phosphate buffer. The pH was adjusted with concentrated acid or base, and the spectra were recorded. A maximum was observed to occur near 510 nm. The dye is red at pH 9, orange at pH 10, and yellow at pH 11. The pK is 10.

Figure 10:
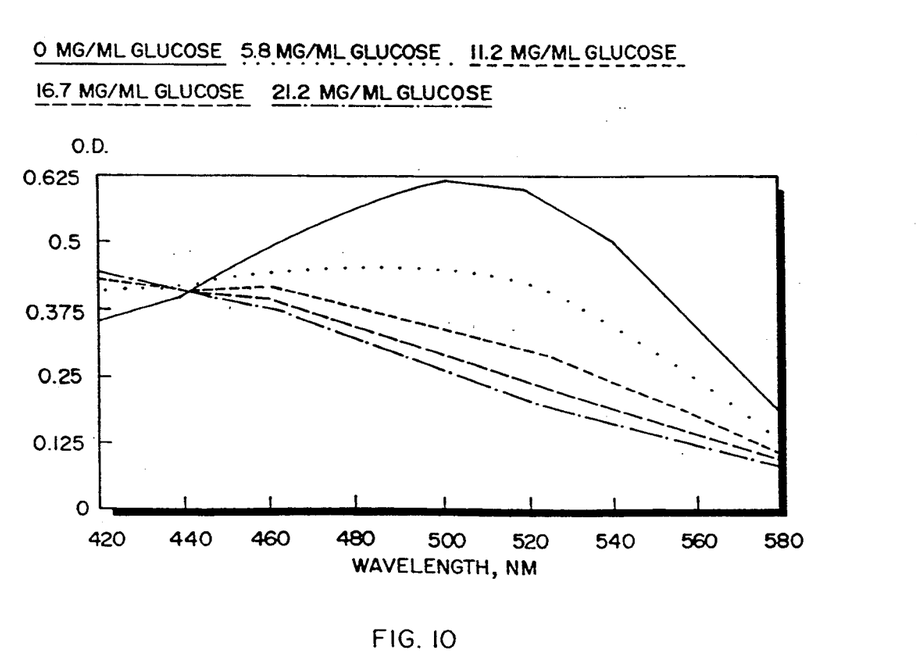
Figure 11:
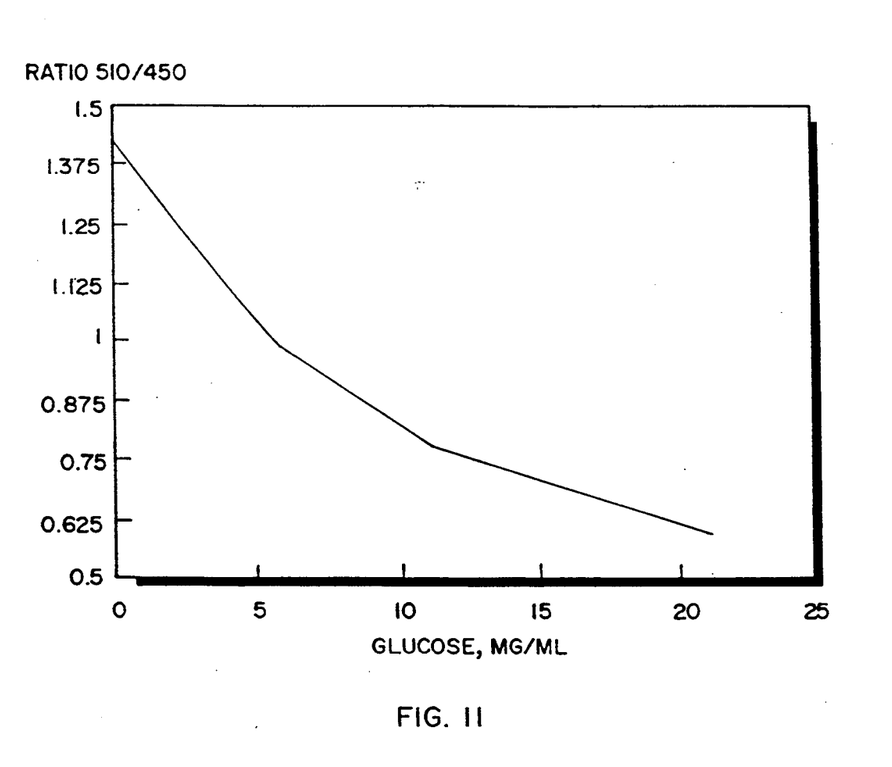

At pH 10, this dye provides a visual indication of reaction with glucose. At a glucose concentration of 15 mg/ml, the dye changes from orange to yellow. Spectra of the dye, shown in FIG. 10, were recorded after titration with 1 M glucose as described in Example 1. Both working solutions contained 0.05 M phosphate buffer, and maintained at pH 10.0. For comparison with previous figures, the ratio of the absorbance at 510 nm to that at 450 nm is also shown in FIG. 11.

The dye is fluorescent. The fluorescence undergoes a change in intensity with addition of glucose.

The dye may be adsorbed to cationic supports to make a glucose test paper. 1.5% polyethyleneimine (PEI), pH 3.5, which contains primary, secondary, and tertiary amines providing cationic charges capable of bonding acid groups of the dye, was crosslinked with 0.5% glutaraldehyde, and dried on filter paper. The prepared paper was soaked in the dye and washed with buffer at pH 10. The paper appeared orange due to the presence of the ionically bonded dye. The paper turned yellow upon treatment with glucose at pH 10. On washing with buffer at pH 10, the orange color returned.

As an alternative to ionic bonding, the carboxy-terminated dye can also be covalently bonded to polyethyleneimine using the water-soluble carbodiimide 1-ethyl-3(3-dimethylaminopropyl) carbodiimide HCl, following the method outlined in XLIV K. Mosbach, *Methods in Enzymology* 53 (1976). To accomplish this, the dye was coupled to an excess of PEI with the carbodiimide at pH 8.3, and then dialyzed for 24 h.

A slight red shift was observed in the spectra of the coupled dye, but the spectra and glucose response were similar to that of the uncoupled dye. The pK of the coupled dye was 10.4.

The terms and expressions which have been employed are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of detecting the presence of vicinal polyhydroxyl compounds in a solvent, comprising the steps of:
   a. establishing the emission characteristics, as a function of polyhydroxyl-compound concentration, of a dye compound comprising a binding moiety selected from the group consisting of boronic acid, boronate ion, arsenious acid, arsenite ion, telluric acid, tellurate ion, germanic acid and germanic ion, covalently linked to a chemical group such that the compound exhibits the properties of a fluorescent dye and wherein binding of said compound to a compound containing vicinal hydroxyl groups results in quantitative attenuation of dye properties:
   b. contacting said solvent with a sample carrier;
   c. introducing said dye into said solvent;
   d. without removing the unbound dye, determining the concentration of polyhydroxyl compound by measuring at least one characteristic of the emitted radiation, the characteristic being selected from the intensity and wavelength.

2. A method of detecting the presence of vicinal polyhydroxyl compounds in a solvent, comprising the steps of:
   a. contacting said solvent with a sample carrier;
   b. introducing into said solvent a fluorescent dye compound comprising a binding moiety selected from the group consisting of boronic acid, boronate ion, arsenious acid, arsenite ion, telluric acid, tellurate ion, germanic acid and germanate ion, covalently linked to a chemical group such that the compound exhibits the properties of a fluorescent dye and wherein biding of said compound to a compound containing vicinal hydroxyl groups results in attenuation of dye properties;

c. without removing the unbound dye, measuring at least one characteristic of the emitted radiation, the characteristic being selected from the intensity and wavelength, wherein the step of introducing said dye compound into said solvent is accomplished by means of test paper to which said dye compound has been bound.

3. A method of detecting the presence of vicinal polyhydroxyl compounds in a solvent, comprising the steps of:

a. contacting said solvent with a sample carrier;

b. introducing into said solvent a fluorescent dye compound comprising a binding moiety selected from the group consisting of boronic acid, boronate ion, arsenious acid, arsenite ion, telluric acid, tellurate ion, germanic acid and germanate ion, covalently linked to a chemical group such that the compound exhibits the properties of a fluorescent dye and wherein biding of said compound to a compound containing vicinal hydroxyl groups results in attenuation of dye properties;

c. without removing the unbound dye, measuring at least one characteristic of the emitted radiation, the characteristic being selected from the intensity and wavelength, wherein the step of introducing said dye compound into said solvent is accomplished by means of fiber-optic material to which said dye compound has been bound.

4. The method of claim 1 wherein said binding moiety is selected from the group consisting of m-aminophenylboronic acid, m-aminophenylboronate, m-aminophenylarsenious acid, m-aminophenylarsenite, m-aminophenyltelluric acid, m-aminophenyltellurate, m-aminophenylgermanic acid and m-aminophenylgermanate.

5. A method of detecting the presence of vicinal polyhydroxyl compounds in a solvent, comprising the steps of:

a. contacting said solvent with a sample carrier;

b. introducing into said solvent a fluorescent dye compound comprising a binding moiety selected from the group consisting of boronic acid, boronate ion, arsenious acid, arsenite ion, telluric acid, tellurate ion, germanic acid and germanate ion, covalently linked to a chemical group such that the compound exhibits the properties of a fluorescent dye and wherein biding of said compound to a compound containing vicinal hydroxyl groups results in attenuation of dye properties;

c. without removing the unbound dye, measuring at least one characteristic of the emitted radiation, the characteristic being selected from the intensity and wavelength, wherein the dye compound is prepared by diazotizing an aryl compound selected from the group consisting of m-aminophenylboronic acid, m-aminophenylboronate, m-aminophenylarsenious acid, m-aminophenylarsenite, m-aminophenyltelluric acid, m-aminophenyltellurate, m-aminophenylgermanic acid and m-aminophenylgermanate, and coupling said diazotized aryl compound to an electron donating species, such that the compound formed thereby exhibits the properties of a dye and wherein binding of said compound to a polyhydroxyl compound results in attenuation of the dye properties of said compound.

6. The method of claim 5 wherein said electron donating species is selected from the group consisting of m-aminophenylboronic acid, m-aminophenylboronate, m-aminophenylarsenious and animated polystyrene polymers and copolymers.

7. The method of claim 1 wherein said one or more polyhydroxyl compound are monosaccharides or disaccharides.

8. A method of detecting the presence of vicinal polyhydroxyl compounds in a solvent, comprising the steps of:

a. contacting said solvent with a sample carrier;

b. introducing into said solvent a dye compound comprising a binding moiety selected from the group consisting of boronic acid, boronate ion, arsenious acid, arsenite ion, telluric acid, tellurate ion, germanic acid and germanate ion, covalently linked to a chemical group such that the compound exhibits the properties of a dye and wherein binding of said compound to a compound containing vicinal hydroxyl groups results in attenuation of dye properties;

c. exposing said sample carrier and said solvent to radiation; and d. measuring the intensity of the radiation passing through the sample relative to that impinging on the sample, wherein the step of introducing said dye compound into said solvent is accomplished by means of polymeric material to which said dye compound has been bound.

9. The method of claim 8 wherein said polymeric material is test paper.

10. A method of detecting the presence of vicinal polyhydroxyl compounds in a solvent, comprising the steps of:

a. contacting said solvent with a sample carrier;

b. introducing into said solvent a dye compound comprising a binding moiety selected from the group consisting of boronic acid, boronate ion, arsenious acid, arsenite ion, telluric acid, tellurate ion, germanic acid and germanate ion, covalently linked to a chemical group such that the compound exhibits the properties of a dye and wherein binding of said compound to a compound containing vicinal hydroxyl groups results in attenuation of dye properties;

c. exposing said sample carrier and said solvent to radiation; and d. measuring the intensity of the radiation passing through the sample relative to that impinging on the sample, wherein the step of introducing said dye compound into said solvent is accomplished by means of fiber-optic material to which said dye compound has been bound.

11. A method of detecting the presence of vicinal polyhydroxyl compounds in a solvent, comprising the steps of:

a. contacting said solvent with a sample carrier;

b. introducing into said solvent a dye compound comprising a binding moiety selected from the group consisting of boronic acid, boronate ion, arsenious acid, arsenite ion, telluric acid, tellurate ion, germanic acid and germanate ion, covalently linked to a chemical group such that the compound exhibits the properties of a dye and wherein biding of said compound to a compound containing vicinal hydroxyl groups results in attenuation of dye properties;

c. exposing said sample carrier and said solvent to radiation; and d. measuring the intensity of the radiation passing through the sample relative to that impinging on the sample, wherein the dye compound is prepared by diazotizing an aryl compound selected from the group consisting of m-aminophenylboronic acid, m-aminophenylboronate, m-aminophenylarsenious acid, m-aminophenylarsenite, m-aminophenyltelluric acid, m-aminophenyltellurate, m-aminophenylgermanic acid and m-aminophenylgermanate, and coupling said diazotized aryl compound to an electron donating species, such that the compound formed thereby exhibits the properties of a dye and wherein binding of said compound to a polyhydroxyl compound results in attenuation of the dye properties of said compound.

12. The method of claim 11 wherein said electron donating species is selected from the group consisting of m-aminophenylboronic acid, m-aminophenylboronate, and animated polystyrene polymers and copolymers.

* * * * *